United States Patent [19]

Gadzala et al.

[11] 3,951,156
[45] Apr. 20, 1976

[54] CURL RETENTION AND MECHANICAL PROPERTIES OF HAIR BY GLYOXAL-PENTAERYTHRITOL COMPLEX

[75] Inventors: Antoni E. Gadzala, Oakville, Canada; James F. Kinney, Ramsey, N.J.; Gary H. Henderson, Middletown, N.Y.

[73] Assignee: Avon Products, Inc., Suffern, N.Y.

[22] Filed: May 22, 1974

[21] Appl. No.: 472,364

[52] U.S. Cl. ............................. 132/7; 424/DIG. 1; 424/47; 424/70; 424/71
[51] Int. Cl.[2] .......................................... A45D 7/04
[58] Field of Search .................. 424/70, 71, DIG. 1, 424/47; 132/7

[56] References Cited
UNITED STATES PATENTS
3,650,280  3/1972  Roberts et al. ................... 424/71 X

OTHER PUBLICATIONS

Chemical Abstracts, Vol. 58, Col. 1351g, (1963).

*Primary Examiner*—Sam Rosen
*Assistant Examiner*—Vera C. Clarke
*Attorney, Agent, or Firm*—Pennie & Edmonds

[57] ABSTRACT

A composition and method for using the same which improves curl retention and mechanical properties of human hair. More particularly, hair dressing compositions containing a complex of glyoxal and pentaerythritol and an inert cosmetic carrier are found to enhance the curl retention and mechanical properties of the hair while not causing a substantial color change in bleached or dyed hair.

11 Claims, No Drawings

CURL RETENTION AND MECHANICAL PROPERTIES OF HAIR BY GLYOXAL-PENTAERYTHRITOL COMPLEX

BACKGROUND OF THE INVENTION

Hair dressing compositions of various forms have been used to alter the appearance and physical properties of human hair. Compositions have been proposed and have been commercially available which are directed to improving one or more hair properties such as curl retention, manageability, and mechanical strength which are commonly desired in the beautification of the hair.

It is well known that hair texture varies with the individual. This variation can be characterized as ranging from coarse, thick hair to the other extreme of fine, limp hair. In attempts to style various hair textures, great difficulties have been encountered due to these variations of texture and to the lack of manageability of the hair to retain the styles given. Hair that has been over-processed by various chemical treatments, as for instance by tinting, bleaching, straightening and the like, for a number of times usually is damaged and no longer retains the style which is desired. The damaged hair has lost body, and normally hangs limp and does not have good appearance.

Many conditioners have been proposed, but few of them function to increase both the curl retention and the mechanical properties such as strength, elasticity, etc., of the hair. Treatment of the hair to improve both mechanical properties and curl retention has been suggested by the use of compositions containing glyoxal alone or condensation products of glyoxal which are polymerizable. These materials have the disadvantage of causing color shifts in previously dyed or bleached hair and, therefore, are unacceptable.

SUMMARY OF THE INVENTION

It has now been found that hair grooming compositions containing a complex of glyoxal and pentaerythritol in a cosmetic carrier material can be applied to the hair to impart increased mechanical strength, curl retention, and elasticity which allow the hair to be groomed in the desired manner without causing a color shift of the hair fibers.

DETAILED DESCRIPTION OF THE INVENTION

The enhancement of the physical properties of hair fibers, such as curl retention, elasticity and mechanical properties while substantially maintaining the color of the hair has been unexpectedly accomplished by the application to the hair fibers of the hair grooming composition containing the complex of glyoxal and pentaerythritol in a cosmetic carrier material.

The complex of glyoxal and pentaerythritol forming the essential element of the instant invention is formed by mixing the two compounds in molar ratios of approximately 2:1 to 1:2 with approximately equal molar quantities being preferred. The mixing is preferably done with the aid of heat and in an acidic media. The compounds are normally mixed in an aqueous solution and the complex formed is readily usable in such form. While the exact nature of the complex is unknown and not clearly understood, it is believed to have the form of a hemiacetal; an acetal; condensation products of the acetal such as its dimer or trimer, as well as mixtures of these forms. The hemiacetal form of the complex is postulated to have a structural formula of

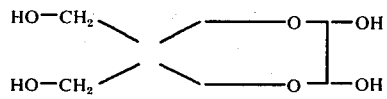

while the acetal form is postulated to be

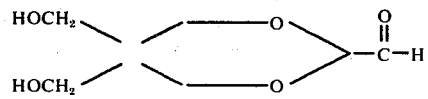

It has been found that aqueous solutions containing the complex of glyoxal and pentaerythritol are stable for long periods of time and, therefore, are readily usable in commerically acceptable compositions.

The glyoxal-pentaerythritol complex can be incorporated into hair grooming compositions in concentrations of from about 1 to about 60 percent and preferably from about 2 to about 20 percent of the hair grooming composition being used.

The complex of glyoxal and pentaerythritol can be incorporated into various nontoxic cosmetic carrier materials well known to those skilled in the art. These carrier materials in which the complex can be incorporated include the inert carriers of water, $C_1$–$C_5$ alcohols, such as methanol, ethanol, and propanol, isopropanol, t-butanol and the like as well as polyhydric $C_1$–$C_5$ alcohols such as ethylene glycol, 1,3-propanediol and the like, water and $C_1$–$C_5$ alcohol mixtures, and animal, vegetable and mineral oils.

The composition may contain, in their usual amounts, additional ingredients such as buffering agents, surfactants, emulsifiers, fillers, foaming agents, stabilizers, thickeners, and the like which are well known to those skilled in the art. The specific additional ingredients or combination of ingredients to be added will depend upon the particular end use of the composition. It is well within the knowledge of the cosmetic chemist to add those additional ingredients deemed necessary to formulate the particular grooming composition desired.

The complex can be applied to the hair in a wide variety of hair grooming forms including shampoos, conditioners to be used prior to or subsequent to shampooing, setting lotions and hair dressing compositions. As stated above, each of these compositions may require the incorporation of additional ingredients noted to formulate the particular grooming composition desired. The addition of said ingredients and the amounts depend merely upon the particular hair grooming formulation desired and is well within the knowledge of the cosmetic chemist and do not require further discussion.

The pH of the final composition can be alkaline or acidic with a pH of from about 3 to about 8 being preferred and from about 4 to about 7 being most preferable. The pH adjustment may be made by the addition of small amounts of base such as sodium hydroxide, calcium hydroxide, potassium hydroxide and the like or an organic $C_1$–$C_5$ acid such as acetic acid, formic acid, and the like, or an inorganic acid such as sulfuric, hydrochloric, phosphoric acid and their equivalents.

Hair grooming compositions containing the active glyoxal-pentaerythritol complex can be applied to the human hair in any of the well known hair dressing manners, such as by hand or spray applications. The composition can be sprayed on the hair from a spraying bottle or an aerosol container. When the composition is applied via an aerosol container, the composition may contain an aerosol propellant such as one of the halogenated hydrocarbons known in the trade as Freon materials which are trichlorofluoromethane, dichlorodifluoromethane, dichlorodifluoroethane, dichlorotetrafluoroethane, and the like as well as nitric oxide, carbon dioxide and the like. Alternately, compositions may be applied to the hair by hand. The composition is normally rubbed into the hair to cause substantial uniform distribution. Such application can be safely done because the complex disclosed herein is nontoxic to humans.

Hair grooming compositions containing the complex of this invention are allowed to remain on the hair for a time sufficient to cause an increase in curl retention, elasticity and mechanical strength of the hair fibers. This time is normally between 3 to 15 minutes with between 5 and 10 minutes usually giving satisfactory results. When preconditioners or shampoos are used, these are rinsed in the normal manner after being allowed to remain on the hair for the effective time period. When the glyoxal-pentaerythritol complex is incorporated into a hair setting composition or a hair dressing composition the compositions are used within the normal manner and rinsing is not required.

It has further been found that the treatment of the hair with glyoxal-pentaerythritol complexes can be further enhanced by either pretreating or simultaneously treating the hair with any of the well known hair swelling materials. Such materials include urea, thiourea, thioglycollic acid, cyanoguanidine, guanidine, arginine, invert sugars and various other well known disulfide reducing materials which are applicable to hair.

The following examples herein disclosed are for illustrative purposes only and are not meant to be limiting upon the inventive concept except as set forth in the appended claims. All parts and percentages are by weight unless otherwise indicated.

EXAMPLE I

A preshampoo conditioner comprising

| | |
|---|---|
| Glyoxal - Pentaerythritol Complex | 20 Parts |
| Polyoxyethylene (20) sorbitan monolaurate (Tween 20) | 1 |
| Water | q.s. |
| pH = 7 | | was applied to previously dyed hair by hand applications and allowed to remain thereon for about five minutes. A commercial shampoo was then applied and used in the normal manner. The hair was then rinsed and set in the desired style.

The treated hair was found to have increased curl retention and mechanical properties in comparison to the hair prior to treatment. No color shift was observed.

EXAMPLE II

A hair shampoo composition comprising

| | |
|---|---|
| Glyoxal - Pentaerythritol | 20 parts |
| Triethanolamine lauryl sulfate | 16 |
| Lauroyl diethanolamide | 4 |
| Water | q.s. |
| pH = 7.5 | | was worked into previously dyed hair, allowed to remain on the hair for 5 to 10 minutes and then used in a normal shampooing manner.

The resultant hair was found to have increased body while no color shift was observed.

EXAMPLE III

A hair conditioning composition comprising

| | |
|---|---|
| Glyoxal - Pentaerythritol | 10 parts |
| Polyvinylpyrolidone | 2 |
| Coconut oil derivative (Neobee 20) | 3 |
| Crosslinked polyacrylic acid; CAS No. PM 9007-16-3 (Carbopol 934) | 1 |
| Triethanolamine | 1 |
| Liquid multisterol extract (Amerchol L-101) | 2 |
| $H_2O$ | q.s. |
| pH = 6 | | was applied to the hair after shampooing and allowed to remain thereon for approximately 5 minutes. The hair was then rinsed free of conditioning composition and then set in the desired style.

The treated hair had improved curl retention and mechanical properties in comparison to unconditioned hair.

EXAMPLE IV

A hair conditioning composition described in Example III was used in the same manner as above but without rinsing the hair free of the conditioning composition. Similar results were obtained.

EXAMPLE V

A hair setting composition comprising

| | |
|---|---|
| Glyoxal - Pentaerythritol Complex | 10 Parts |
| Ethyl ester of polyvinyl methyl ether/maleic anhydride copolymer; RD No. 977056-77-1 (Gantrez ES-225) | 4 |
| 2-amino-2-methyl-1,3-propanediol | 0.2 |
| Ethanol | 21 |
| Water | q.s. |
| pH = 4 | | was applied after shampooing to previously dyed hair. The hair was set to the desired style in the normal manner.

The hair was observed to have increased curl retention and mechanical strength while no color shift was observed

EXAMPLE VI

The hair setting composition of Example V was applied to the hair in the same manner as described above except that a pretreatment lotion containing thioglycollic acid as the disulfide reducing agent was applied prior to application of the hair setting composition.

The hair was found to have superior curl retention and mechanical properties without any observable color shift.

EXAMPLE VII

A hair dressing composition comprising

| | |
|---|---|
| Glyoxal - Pentaerythritol Complex | 5 Parts |
| Stearic Acid | 6 |
| Triethanolamine | 1.5 |
| Mineral oil | 40 |
| $H_2O$ | q.s. |
| pH = 6 | | was used daily by applying a small amount to the hair and working it in.

The hair was observed to have improved body, and mechanical properties over untreated hair. No color shift was observed in dyed hair.

EXAMPLE VIII

An aerosol hair dressing composition comprising

| | |
|---|---|
| Glyoxal - Pentaerythritol | 10 Parts |
| Stearic Acid | 6 |
| Triethanolamine | 1.5 |
| Mineral dOil | 20 |
| Dichlorotetrafluoroethane (Freon 114) | 15 |
| $H_2O$ | q.s. |
| pH = 7 | | was used daily by spraying a small amount on the hair.

The hair was observed to have increased body, and mechanical properties over untreated hair. No color shift was observed in dyed hair.

The pH in each of the foregoing examples was adjusted with standardized sodium hydroxide or acetic acid as required.

It will be understood that it is intended to cover all changes and modifications of the examples of the invention herein chosen for the purpose of illustration which do not constitute departures from the spirit and scope of the invention.

What is claimed is:

1. A process of grooming hair to cause improved curl retention and mechanical properties while substantially maintaining the hair color comprising applying to the hair an effective amount of a hair grooming composition containing an inert cosmetic carrier and from about 1 to about 60 percent of the total composition of glyoxal-pentaerythritol complex having a molar ratio of about 2:1 to 1:2, said composition having a pH of from about 3 to about 8, and allowing said composition to remain thereon for a time sufficient to treat the hair.

2. A process of grooming hair to cause improved curl retention and mechanical properties while substantially maintaining the hair color comprising applying to the hair an effective amount of a hair grooming composition having a pH of from about 3 to about 8 containing an inert cosmetic carrier and from about 1 to about 60 percent of the total composition of glyoxal-pentaerythritol complex of molar ratios of about 2:1 to 1:2, allowing the composition to remain thereon for a period of time sufficient to treat the hair, and rinsing the spent composition from the hair.

3. The process of claim 2 wherein the hair is subsequently set, combed or brushed into the form desired.

4. The process of claim 2 wherein the composition is applied to the hair by hand application.

5. The process of claim 1 wherein the composition is applied to the hair by aerosol spray application.

6. A process of grooming hair to cause improved curl retention and mechanical properties while substantially maintaining hair color comprising applying to the hair an effective amount of a hair grooming composition having a pH of about 3 to about 8 comprising an inert cosmetic carrier selected from the group consisting of water, a $C_1$–$C_5$ alcohol, mixtures of water and a $C_1$–$C_5$ alcohol, vegetable oil, animal oil, and mineral oil, having dispersed therein from about 1 to about 60 percent of the total composition of glyoxal-pentaerythritol complex of molar ratio of about 2:1 to about 1:2, and allowing said composition to remain on the hair for a sufficient time for treatment.

7. A process according to claim 6 wherein the pH of the composition applied is from about 4 to about 7.

8. The process of claim 6 wherein the composition applied contains from about 2 to about 20 percent of the glyoxal-pentaerythritol complex.

9. The process of claim 6 wherein the hair is subsequently set, combed, or brushed into the form desired.

10. The process of claim 6 wherein the composition is applied to the hair by hand application.

11. The process of claim 6 wherein the composition is applied to the hair by aerosol spray application.

* * * * *